(12) United States Patent
Stjernschantz et al.

(10) Patent No.: US 6,495,563 B1
(45) Date of Patent: Dec. 17, 2002

(54) METHOD AND COMPOSITION FOR PREVENTION OF SCAR FORMATION IN GLAUCOMA FILTRATION BLEB AND DRAINAGE FISTULA

(75) Inventors: Johan Stjernschantz, Uppsala (SE); Bahram Resul, Uppsala (SE)

(73) Assignee: Synphora AB, Uppsala (SE)

( * ) Notice: Subject to any disclaimer, the term of this patent is extended or adjusted under 35 U.S.C. 154(b) by 0 days.

(21) Appl. No.: 09/913,849
(22) PCT Filed: Feb. 23, 2000
(86) PCT No.: PCT/SE00/00357
§ 371 (c)(1), (2), (4) Date: Nov. 2, 2001
(87) PCT Pub. No.: WO00/50040
PCT Pub. Date: Aug. 31, 2000

(30) Foreign Application Priority Data

Feb. 25, 1999 (SE) ................................................ 9900672

(51) Int. Cl.⁷ ............................................. A61K 31/215
(52) U.S. Cl. ...................... 514/310; 514/573; 514/912
(58) Field of Search ................................. 514/530, 573, 514/912

(56) References Cited

U.S. PATENT DOCUMENTS

| 3,981,880 A | 9/1976 | Schneider |
| 5,739,113 A | 4/1998 | Lee |

FOREIGN PATENT DOCUMENTS

| EP | 097023 | 12/1983 |
| EP | 242580 | 10/1987 |
| EP | 366279 | 5/1990 |
| EP | 455264 | 11/1991 |
| GB | 1532009 | 11/1978 |
| WO | 90/02553 | 3/1990 |
| WO | 95/26729 | 10/1995 |
| WO | 96/09055 | 3/1996 |

*Primary Examiner*—Zohreh Fay
(74) *Attorney, Agent, or Firm*—Banner & Witcoff, Ltd.

(57) ABSTRACT

This invention is related to a method whereby scar formation in the drainage fistula and subconjunctival bleb created during and after glaucoma surgery using a prostaglandin subtype A or J.

12 Claims, 5 Drawing Sheets

$^{15\Delta}$-PGJ$_2$

Figure 1:
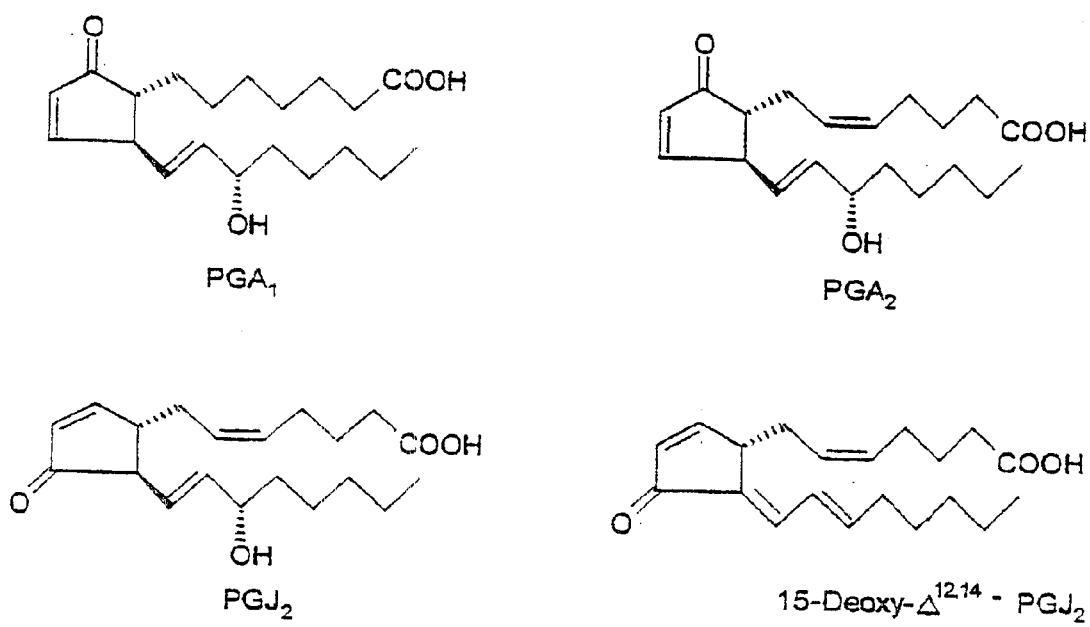

METHOD AND COMPOSITION FOR PREVENTION OF SCAR FORMATION IN GLAUCOMA FILTRATION BLEB AND DRAINAGE FISTULA

This is a U.S. National Phase Application Under 35 USC 371 and applicant herewith claims the benefit of priority of PCT/SE00/00357 filed Feb. 23, 2000, which was published under PCT Article 21(2) in English and Application No. 9900672-8 filed in Sweden on Feb. 25, 1999.

The present invention is related to a method whereby scar formation in the drainage fistula and subconjunctival bleb created during glaucoma surgery can be prevented. The invention is also related to a composition used for prevention of scar formation in the drainage fistula and subconjunctival bleb after glaucoma surgery.

BACKGROUND OF THE INVENTION

Glaucoma is an eye disorder characterized by increased intraocular pressure, excavation of the optic nerve head, and gradual loss of visual field. An abnormally high intraocular pressure is commonly known to be detrimental to the eye, and there are clear indications that in glaucoma the intraocular pressure is the most important factor causing degenerative changes in the retina and the optic nerve head. The exact pathophysiological mechanism of open angle glaucoma is, however, still unknowns. Unless treated glaucoma may lead to blindness, the course of the disease typically being slow with progressive loss of vision.

The intraocular pressure is determined by the rate of production and drainage of aqueous humor in the anterior part of the eye. The aqueous humor is produced by the ciliary processes behind the iris. It then flows through the pupil into the anterior chamber, and normally exits the eye through the trabecular meshwork and Schlemm's canal. However, in open angle glaucoma the resistance to outflow of aqueous humor is increased which causes the intraocular pressure to raise. The intraocular pressure in humans is normally around 12–21 mmHg. At higher pressures there is an increased risk that the eye may be damaged. In one particular form of glaucoma, namely low tension glaucoma, damage may, however, occur at intraocular pressures regarded to be within the normal physiological range. The opposite situation is also known i.e. some individuals may exhibit abnormally high intraocular pressure without any manifest defects in the visual field or optic nerve head. Such conditions usually are referred to as ocular hypertension.

Glaucoma treatment can be given by means of drugs, laser or surgery. Usually surgery is employed only when drug and laser treatments no longer are sufficiently effective. A relatively new medical treatment of glaucoma comprises the use of prostaglandins, which are administered topically on the eye, and reduce the intraocular pressure by enhancing the outflow of aqueous humor. Two such prostaglandin-based glaucoma drugs are currently being marketed in many countries, i.e. latanoprost (Xalatan®) and isopropyl unoprostone (Rescula®), and are extensively used clinically. The use of prostaglandins and derivatives is described in several patents and patent applications e.g. U.S. Pat No. 4,599,353 (Bito), U.S. Pat No. 4,952,581 (Bito), WO89/03384 (Sternschantz and Resul), WO 96/09055 (Sternschantz and Resul), EP 170258 (Cooper), EP 253094 (Goh) and EP 308135 (Ueno). In addition to these patents and patent applications a large number of new patent applications have been filed during the last years. Common for all these patents and patent applications is that they describe the use of prostaglandins for reduction of the intraocular pressure without surgery.

The prostaglandins are fatty acids usually derived from the precursors eicosatrienoic, eicosatetracnoic and eicosapentaenoic acid through metabolic steps involving oxygenation. Naturally occuring prostaglandins typically have the general structure presented below:

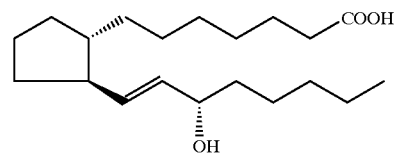

The prostaglandins accordingly carry a cyclopentane ring to which two carbon chains attach, the upper chain usually being called the alpha chain and the lower chain usually being called the omega chain. The prostaglandins are classified in subgroups A, B, C, D, E, F, G, H, I, and J, depending on the structure and the substituents in the cyclopentane ring. The prostaglandins of particular interest in the present invention belong to the subgroups A and J, and their cyclopentane ring configuration is presented below:

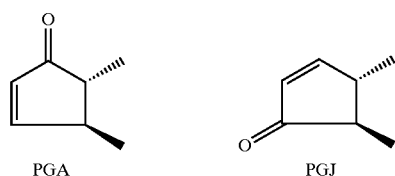

PGA  PGJ

The alpha chain is a 7 carbon carboxy-terminated aliphatic chain whereas the omega chain is an 8 carbon methyl-terminated aliphatic chain. Depending on the number of double bonds in these chains, subscripts of 1 to 3 are given. In prostaglandins with subscript 1, e.g. $PGA_1$, the double bond is situated between carbons 13 and 14 in the omega chain. In prostaglandins with subscript 2, e.g. $PGJ_2$, an additional double bond is situated between carbons 5 and 6 in the alpha chain, and finally in prostaglandins with subscript 3, a third double bond is situated between carbons 17 and 18 in the omega chain. All naturally occuring prostaglandins furthermore carry a hydroxyl group on carbon 15.

Many different techniques have been described for glaucoma surgery. However, all techniques aim at creating a small drainage fistula for the aqueous humor to exit the eye in the vicinity of the trabecular meshwork. Thus the aqueous humor can bypass the trabecular meshwork tissue at Schlemm's canal that usually is clogged in open angle glaucoma. The fluid is directed into a filtration bleb beneath the conjunctiva outside the eye. The most commonly practiced operation technique is called trabeculectomy and usually results in satisfactory pressure lowering of the eye. A very common complication, however, is formation of scar tissue in the filtration bleb, which reduces the drainage capacity of the filtration system created by surgery. The scar formation is mainly due to the proliferation and increased activity of fibroblasts. Consequently the intraocular pressure with time starts to return to pathological levels. Usually the scarring occurs several months Lo yews after surgery, and the use of antimitotic agents such as 5-fluorouracil and Mitomycin C during surgery improves the surgical results. However, Mitomycin C and 5-fluorouracil are very toxic compounds with a narrow therapeutic index, and difficult to use clinically. Late complications such as conjunctival holes may ensue after the use of e.g. Mitomycin C. Thus there is a need for better and safer drugs to be used as a complement to the surgical procedure to prevent the scarring of the filtration system created by surgery.

SUMMARY OF THE INVENTION

The above problems associated with glaucoma surgery are now solved by the present invention as defined in the attached claims, hereby incorporated by reference. The invention is based on the unexpected finding that prostaglandins of type A and J may be highly effective in preventing scar formation that typically occurs after glaucoma surgery, and that the compositions comprising these compounds and the methods described have advantages over the compositions and methods hitherto known.

SHORT DESCRIPTION OF THE DRAWINGS

Figure 2:
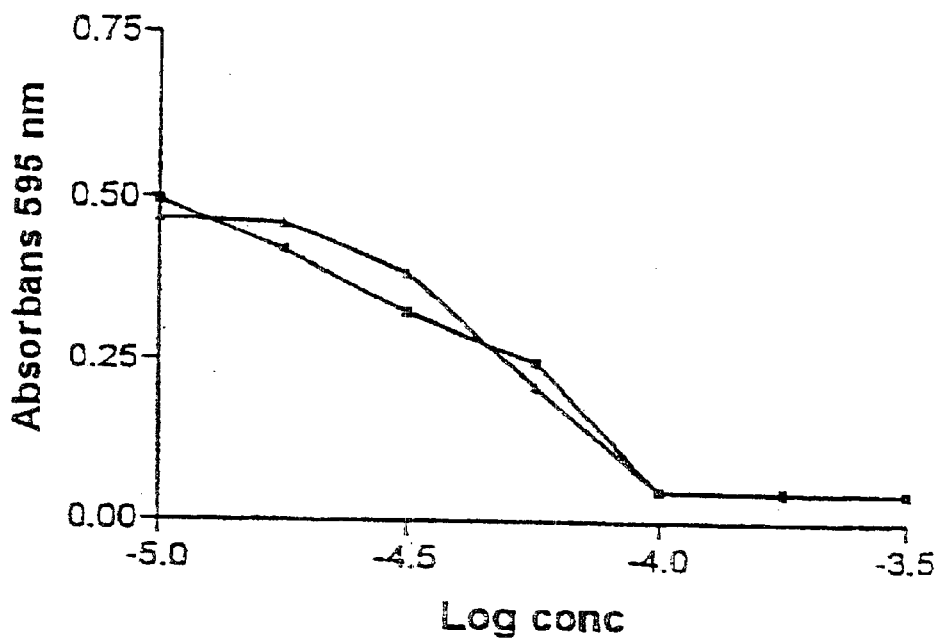
Figure 2:
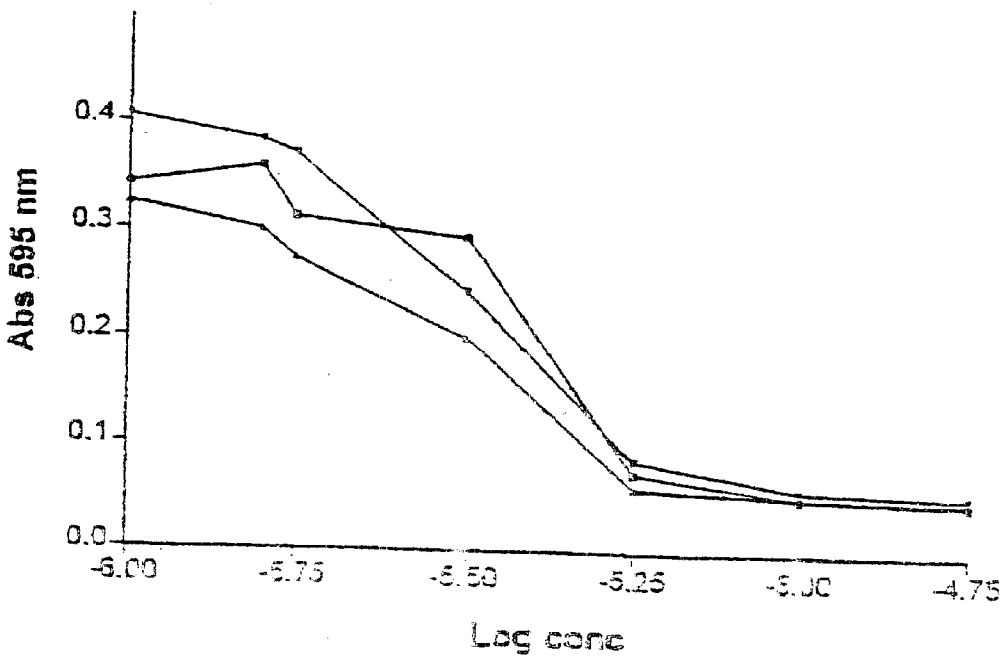
Figure 3:
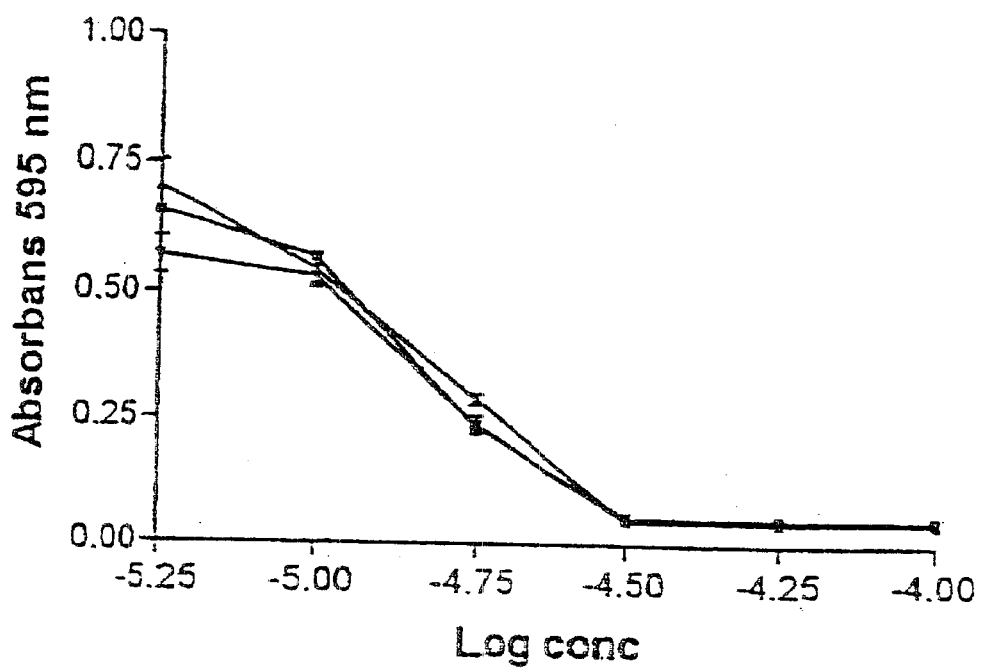
Figure 3:
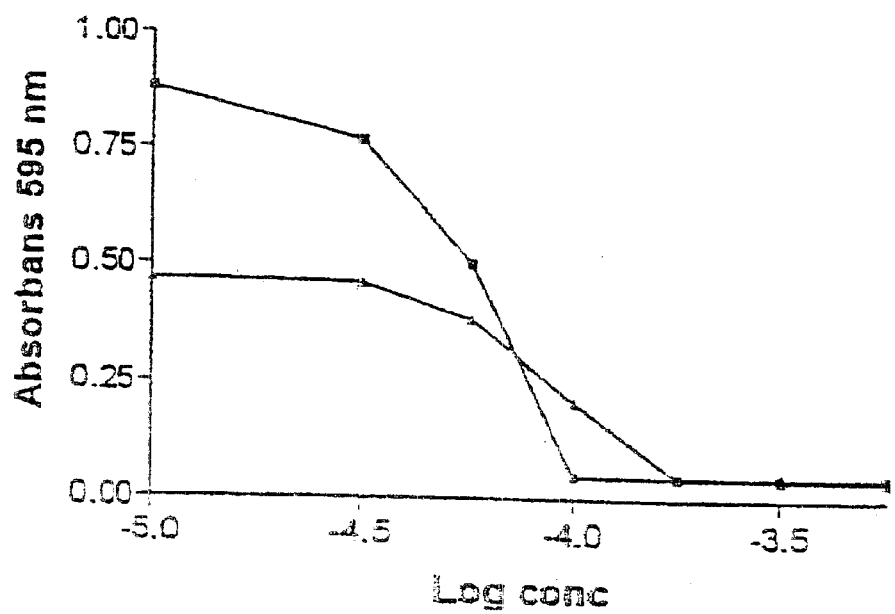
Figure 4:
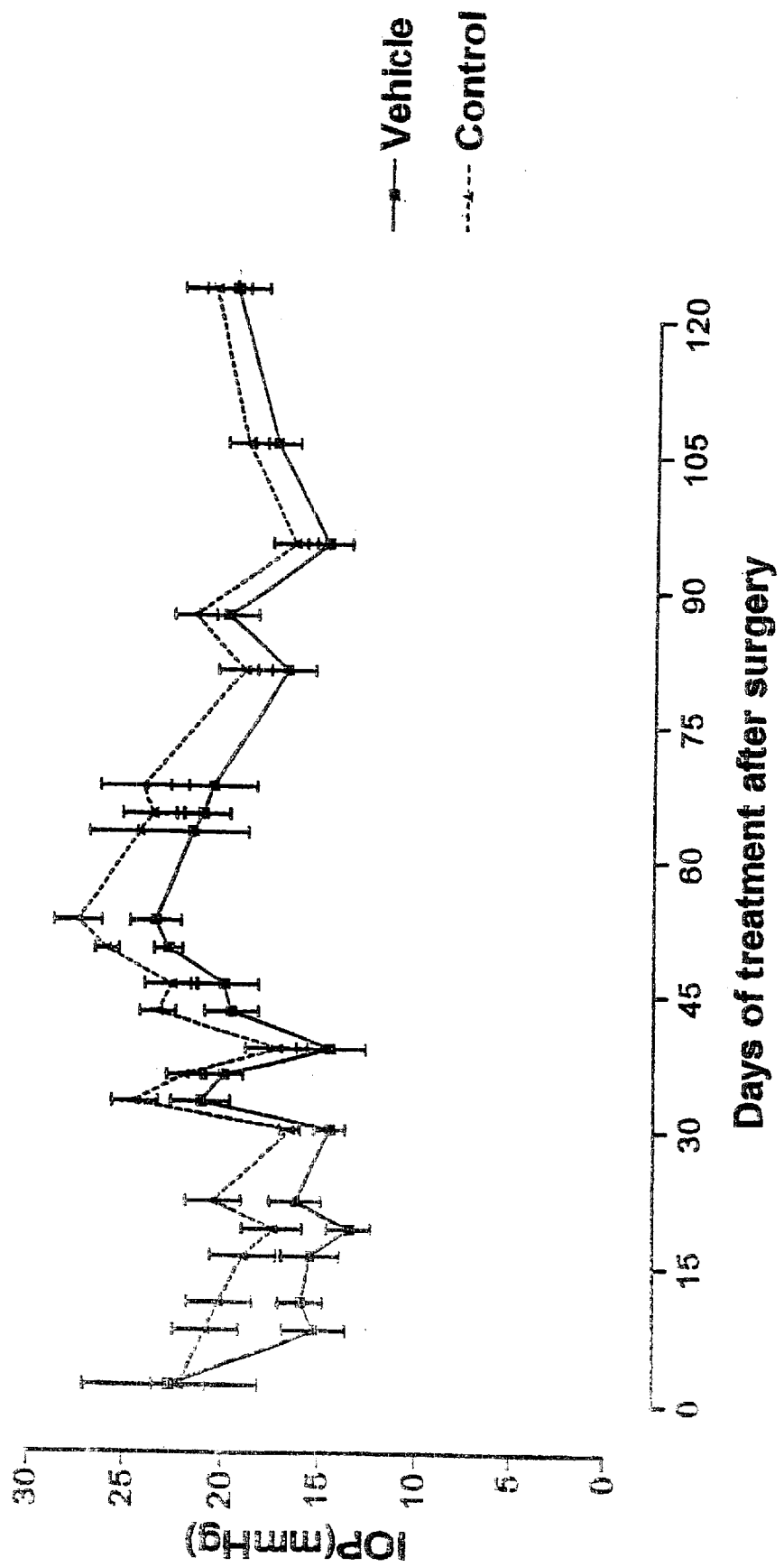

The present invention is described below with reference to the attached drawings, in which FIG. 1 shows the chemical structures of the tested compounds, prostaglandin $A_1$, prostaglandin $A_2$, prostaglandin $J_2$ (PG $J_2$) and 15-deoxy-$\Delta^{12,14}$-prostaglandin $J_2$ ($^{15\Delta}PGJ_2$);

FIG. 2 shows the absorbance at 595 nm (measure of cell number) as a function of the concentration (plotted as negative logarithm) of the test compounds $PGA_1$, and $PGA_2$, FIG. 3 shows the absorbance at 595 nm (measure of cell number) as a function of the concentration (plotted as negative logarithm) of the test compounds $PGJ_2$ and 15-deoxy-$\Delta^{12,14}$-prostaglandin $J_2$ ($^{15\Delta}PGJ_2$), FIG. 4 shows the intraocular pressure in the vehicle-treated operated, and the control eyes of rabbits following trabebeculectomy surgery during four months.

Figure 5:
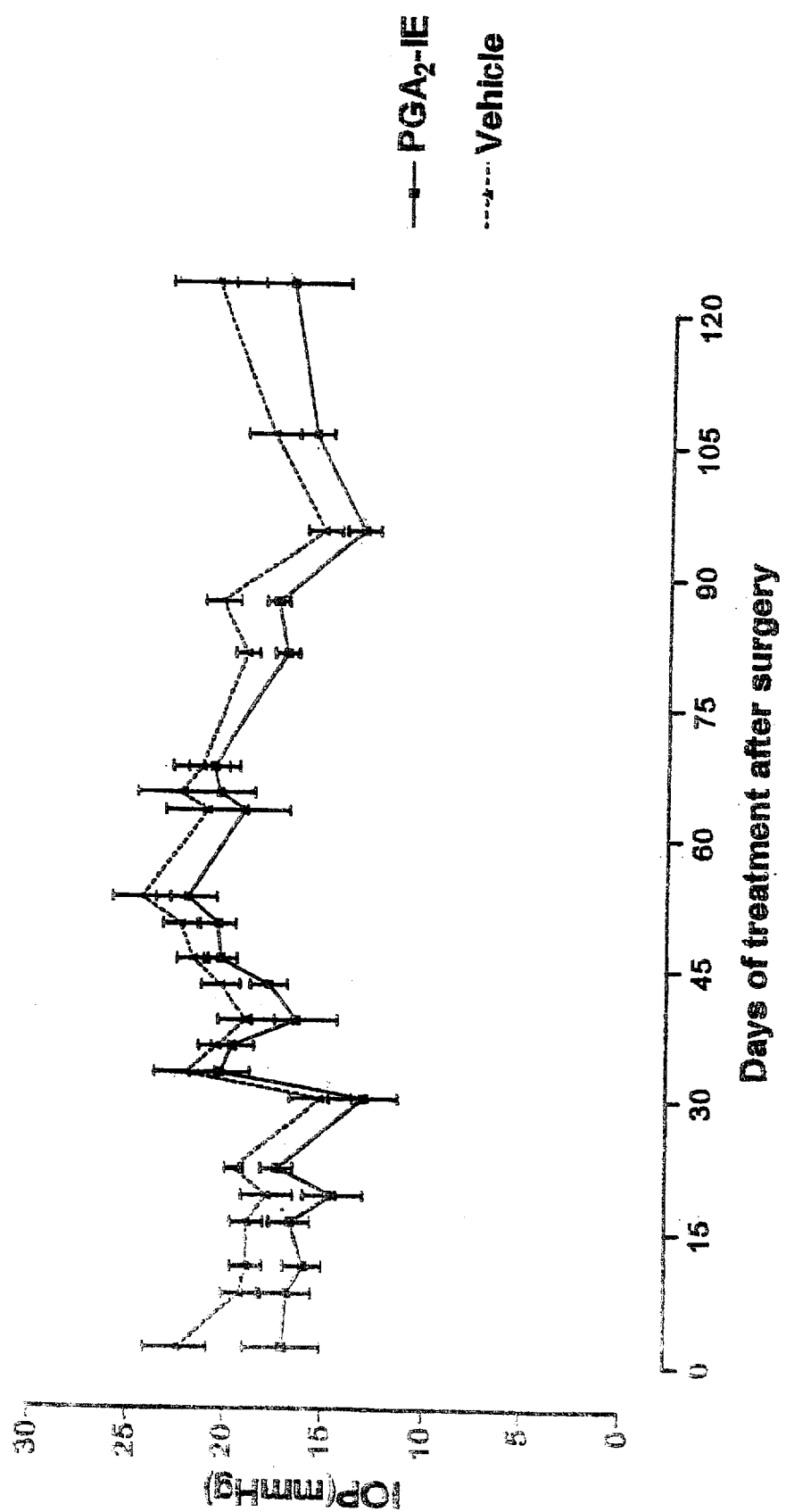

FIG. 5 shows the intraocular pressure in $PGA_2$-IE-treated operated, and the control eyes of rabbits following trabebeculectomy surge during four months.

DESCRIPTION

Experiments performed by the present inventors have shown that specific prostaglandins have a marked antimitotic effect on human fibroblasts in culture. Indeed, at high concentrations these prostaglandins seem to exert even cytotoxic effects, killing fibroblasts. Accordingly, topical treatment of the eye with such prostaglandins after surgery will prevent scarring of the filtration bleb and other parts of the filtration system, and thus help keeping the intraoclar pressure at a desired reduced level.

According to one embodiment of the invention, prostaglandins of the A and J type are used for the treatment of glaucoma after filtration surgery, particularly trabeculectomy, by preventing the proliferation of fibroblasts in the filtration system. The method comprises contacting the surface of the eye, including the filtration bleb, with an effective amount of a composition containing a prostaglandin of the subtype A or J. The composition usually contains 0.1–500 µg, especially 1–30 µg per application of the active substance. The composition is applied topically on the eye 1–3 times daily, or only every second day, or once a week, or possibly intermittently, e.g. for a month and thereafter a few months later again for a month etc.

The prostaglandin derivative is mixed with an ophthalmologically compatible vehicle known per se. Vehicles, which may be employed for preparing compositions according to the present invention comprises aqueous solutions, e.g. physiological saline, oil solutions, creams and ointments. The vehicle may furthermore contain ophthalmologically compatible preservatives such as benzalkonium chloride, inclusion complexes such as cyclodextins, surfactants e.g. polysorbate 80, and liposomes. Polymeres, for example methyl cellulose, polyvinyl alcohol, polyvinyl pyrrolidone, and hyaluronicacid may also be employed; these may be used for increasing the viscosity. Furthermore it is also possible to use soluble or insoluble drug inserts.

One embodiment of the invention comprises ophthalmological compositions, for treatment of glaucoma after trabeculectomy to prevent scaring of the filtration system, which comprise an effective amount of a prostaglandin of the A or J type, and an ophtalmologically compatible carrier. The effective amount usually comprises a dose of about 0.1–500 µg in about 10–50 µl of the composition.

According to another embodiment, the invention relates to the use of a prostaglandin analogue for the preparation of a medicament for the treatment of glaucoma after fistulating surgery to prevent scar formation in the filtration system.

It should be emphasized that the present invention is not aimed at treating open angle glaucoma without surgery ba using prostaglandins of the A and J type for the intraocular pressure reducing effect of these prostaglandins, an invention described e.g. in U.S. Pat No. 4,883,819 (Bito), but solely for preventing the scar formation that occurs in the filtration bleb and fistula created by surgery.

EXAMPLES

The invention is exemplified by the following non-limiting examples:

The following prostaglandins, purchased from Cayman Chemicals, Ann Arbor, Mich., USA, and Biomol Feinchemikalien GmbH, Hamburg, Germany were used in the experiments: prostaglandin $A_1$ ($PGA_1$), prostaglandin $A_2$ ($PGA_2$), prostaglandin $J_2$ ($PGJ_2$) and 15-deoxy-$\Delta^{12,14}$-prostaglandin $J_2$ (15-$\Delta^{12,14}$-$PGJ_2$). The chemical structures of the test compounds are depicted in FIG. 1. All test compounds were stored at –20° C., and fresh solutions containing the appropriate concentrations of the test compounds were made every second day. The test compounds were initially dissolved in ethanol and then diluted in the culture medium.

Human fibroblasts were used at passage 22–24. The culture medium consisted of DMEM with 10% fetal calf serum and 50 µg/ml gentamycin. Around 10,000 cells were seeded into each well of 48 well microtiter plates. The total volume of culture medium was about 250 µl/well. The cells were incubated at 37° C. with 5% $CO_2$ humidified air. The culture medium was changed every second day, and at the same time new, freshly prepared prostaglandin was added to the medium. The test compounds were investigated at several concentrations in the range of $10^{-6}$ to $10^{-3}$ Moles/l. Preliminary studies indicated that concentrations lower than $10^{-6}$ M had no effect. The concentrations in the figures depicting the results are expressed as the negative logarithm The culture medium alone served as control. After 5–7 days of culture the experiment was terminated by fixation of the cells in 1% glutaraldehyde. The cells were then stained with 0.1% crystal violet, and the stain was eluted with 2.5% sodium lauryl sulphate. The absorbance of the colored solutions was determined spectrophotometrically. Each experiment was performed at least in duplicate.

The results of the ex tents are depicted in FIGS. 2–3. It can be seen that all test compounds, $PGA_1$, $PGA_2$, $PGJ_2$ as well as 15-deoxy-$\Delta^{12,14}$-$PGJ_2$ effectively reduced the cell number of the cultures as shown by the decrease in crystal violet absorbance. The control wells (without prostaglandin) exhibited absorbances similar to the lowest concentration tested of the test compounds (not shown in the figures). Although all test compounds exhibited the same absolute efficacy in reducing the cell number, $PGA_2$ appeared to be the most potent one, and exhibited an $EC_{50}$ value of around −5.5 log units corresponding to about $3\times10^{-6}$ Moles/l. The corresponding value of $PGJ_2$ was about −4.75 log units corresponding to about $2\times10^{-5}$ Moles/l, whereas the values of the two other prostaglandin analogues were clearly higher.

Concentrations in the range of $10^{-5}$ to $10^{-4}$ Moles/l are possible to achieve in the filtration bleb under the conjunctiva in vivo, and since these concentrations had marked effect in vitro, it is very likely that even lower concentrations of the test compounds would exbibit beneficial antiproliferative effect on the fibroblasts in the filtration bleb. Thus prostaglandins with the general structure of cyclopentenone such as PGA's and PGJ's seem to have a marked antiproliferative and indeed even cytotoxic effect depending on concentration and this property of these prostaglandins can be used clinically to prevent scaring of the filtration bleb after glaucoma surgery.

Two series of in vivo experiments have been performed in rabbits during the priority year. In the first series of experiments it was demonstrated that the intraocular pressure is maintained at a reduced level after modified trabeculectomy surgery during topical treatment with $PGA_2$-isopropyl ester ($PGA_2$-IE) eye drops, and in the second series of experiments it was shown that in addition to the antiproliferative effect, cyclopentenone prostaglandins also have a marked anti-inflammatory effect in the eye which is advantageous after glaucoma surgery.

Maintenance of the Intraocular Pressure at a Reduced Level after Glaucoma Surgery by Cyclopentenone Prostaglandin Treatment.

Ten New Zealand White adult rabbits underwent modified unilateral trabeculectomy surgery and were treated with corticosteroids and mydriatics postoperatively for about one month according to a clinical protocol. Starting the same day as the surgery was performed, the operated eye in five animals was in addition treated twice daily with $PGA_2$-IE eye drops (10 μg/dose) for 4 months, while in the other five animals the operated eye was treated with vehicle only for the same period of time. The intraocular pressure was measured throughout the treatment period at least every second week. The results are presented in FIGS. 4 and 5, and demonstrate that the intraocular pressure of the operated eyes throughout the treatment period in all animals was maintained at a lower level than in the contralateral (non-operated) control eye. However, with time there was a clear tendency towards better maintenance of the intraocular pressure at a reduced level after surgery in the animals treated with $PGA_2$-IE than in the vehicle control animals. From FIG. 4 it is apparent that the difference in intraocular pressure between the vehicle-treated operated and control eyes steadily diminished with time which was quite opposite to the difference in traocular pressure between the $PGA_2$-IE-treated operated and control eyes in FIG. 5. Thus it appears that even during this short treatment period (4 months) a difference in the level of intraocular pressure reduction between the $PGA_2$-IE treated and vehicle-treated operated eyes is manifested, and at the end of the treatment period the difference in intraocular pressure reduction was statistically significant (p<0.05) (Table 1). It is also evident that the $PGA_2$-IE treatment had no adversarial effects in the eye as there were no signs of local inflammation or increased intraocular pressure during the treatment period that could be attributed to the use of the prostaglandin analogue.

TABLE 1

Intraocular pressure at the end of the 4 month treatment period following surgery.
The operated eyes received $PGA_2$-IE or vehicle, the control eyes received no treatment.

| Treatment group | n | Operated eye (mmHg) | Control eye (mmHg) | Difference (mmHg) |
|---|---|---|---|---|
| $PGA_2$-IE | 5 | 17.2 ± 2.9 | 21.0 ± 2.4 | 3.8 ± 1.0* |
| Vehicle | 5 | 19.8 ± 1.5 | 20.8 ± 1.6 | 1.0 ± 0.3 |

*p < 0.05 when compared to vehicle group

Anti-inflammatory Effect of Cyclopentenone Prostaglandins in the Eye

Ten New Zealand White adult rabbits underwent extracapsular lens extraction in one eye to investigate the effect of $PGA_2$-E on postsurgical inflammation. Lens extraction was used as a model since this procedure is always followed by some inflammatory changes. The contralateral eye was used as an untreated control eye in each animal. The operated eyes were given routine postsurgical treatment with corticosteroids and mydriatics for about one month. From the day after the surgery and for a total of 4 months 5 of the animals were treated with $PGA_2$-IE eye drops twice daily (10 μg/dose) in the operated eye while the contralateral control (non-operated) eye received no treatment. The other 5 animals were treated with the vehicle only twice daily for the same period of time. Surprisingly it was found that only one of the animals receiving $PGA_2$-IE exhibited signs of clear-cut inflammation whereas most of the animals in the vehicle group repeatedly exhibited signs of intraocular inflammation during the 4 month treatment period. The signs of inflammation comprised miosis, iridial hyperemia, flare and fibrin accumulation in the anterior chamber, and additional anti-inflammatory medication had to be given to these animals. Thus $PGA_2$-IE had a remarkable anti-inflammatory effect in the eye. The results are summarized in Table 2.

TABLE 2

Number of animals exhibiting inflammation of the operated eye 2 and 4 months after surgery.

| Treatment group | Time of treatment after surgery | | | |
|---|---|---|---|---|
| | 2 months | | 4 months | |
| | Normal | Inflamed | Normal | Inflamed |
| Vehicle | 0 | 5 | 1 | 4 |
| $PGA_2$-IE | 3 | 2* | 4 | 1 |

*one only slightly inflamed

Since inflammation, which also occurs in the filtering bleb after trabeculectomy surgery, is known to induce fibroblast proliferation and scarring, reduced inflammation is beneficial for keeping the filtering bleb functional.

Accordingly, prostaglandins of the subtypes A and J may be utilised to prevent scar formation of the filtration bleb and drainage fistula after glaucoma surgery. In the exemplification the present inventors have used 4 different cyclopentenone prostaglandins, but also other analogues of the A and J cyclopentenone prostaglandins may be employed. Such analogues comprise e.g. 16,16-dimethyl-PGA$_1$, $\Delta^7$-PGA$_1$, and 16,16-dimethyl-PGA$_2$ as well as PGJ$_1$, $\Delta^{12}$PGJ$_1$ and $\Delta^{12}$PGJ$_2$. There are also other types of derivatives of prostaglandin A and J which are known from the literature and which are obvious candidates to be used according to the present invention. One such group constitutes derivatives with aromatic or non-aromatic ring substituted omega chain as disclosed in PCT application SE89/00475. Also alpha chain modified prostaglandins of the A and J type may be employed. The alpha chain may be straight or branched, saturated or unsaturated with or without carboxylic acid, ester, amide, alcohole or ether moieties. The chain may also contain an aromatic or non-aromatic ring.

In addition to the above, the present inventors have recently found that prostalandins carrying a hydroxyl substituent on carbon 18–20 exhibit no or little initative effect. Such modifications of cyclopentenone prostaglandins may also be employed on the substances according to the present invention.

PGA and PGJ or their analogues may be modified to more lipophilic substances and/or more stable substances e.g. by converting the acid moiety to alcohole, ether, amide or ester. Such esters that may be employed clinically comprise e.g. alkyl esters with 1–10 carbon atoms, and especially short alkyl esters e.g. methyl, ethyl, isopropyl and cyclic esters such as benzyl.

The prostaglandin compounds and their esters or derivatives should be used in a suitable ophthalmologically compatible vehicle. Such vehicles include as described previously aqueous and oil solutions as well as creams and ointments. The vehicle may contain solubilizers and stabilizers such as cyclodextrins, micelle systems, nanoparticles, polymeres and various slow-release systems. The vehicles may or may not contain preservatives such as benzalkonium chloride, chlorhexidine, thiomersal, parabenzoic acid, and other compounds with satisfactory antimicrobial activity.

Accordingly, the prostaglandin of A or J type should be used topically on the eye for different period of time to prevent scar formation in the filtration bleb and drainage fistula after glaucoma surgery. Such treatment may be continuous or intermittent, and it may be necessary also to use the medication only for a relatively short period of time immediately after surgery.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

What is claimed is:

1. A method for the prevention of scar formation in the filtration bleb and drainage fistula after glaucoma surgery performed on a human eye, characterized in that a composition containing a prostaglandin of subtype A or J is brought in contact with the surface of the eye.

2. The method according to claim 1, characterized in that the prostaglandin is PGA or a derivative thereof.

3. The method according to claim 2, characterized in that the prostaglandin is PGA$_2$ or a derivative thereof.

4. The method according to claim 3, characterized in that the prostaglandin is 17-phenyl-18, 19, 20-trinor-PGA$_2$.

5. The method according to claim 1, characterized in that the prostaglandin is PGJ or a derivative thereof.

6. The method according to claim 5, characterized in that the prostaglandin is PGJ$_2$ or a derivative thereof.

7. The method according to claim 6, characterized in that the prostaglandin is 17-phenyl-18,19,20-trinor-PGJ$_2$.

8. The method according to any one of claims 1 through 7, characterized in that the prostaglandin is an ester, especially an isopropyl ester of the prostaglandin in question.

9. The method according to any one of claims 1 through 7 characterized in that the prostaglandin is administered topically to the eye in an amount in the interval of 0.1 to 500 $\mu$g of the active substance per application.

10. The method according to any one of claims 1 though 7 characterized in that the prostaglandin composition is administered topically to the eye 1 to 3 times daily, once every second day, once a week, or intermittently, during administration periods followed by periods when no administration is performed.

11. The method according to any one of claims 1 through 7 characterized in that the prostaglandin is administered topically to the eye with the aid of a slow release drug insert.

12. The method according to any one of claims 1 though 7 wherein the prostaglandin is administered topically to the eye in an amount of 1–30 $\mu$g per application.

* * * * *